United States Patent [19]

Wada et al.

[11] Patent Number: 5,676,996
[45] Date of Patent: Oct. 14, 1997

[54] METHOD OF PREPARING CARRIER FOR BLOOD TREATMENT APPARATUS

[75] Inventors: Takuya Wada, Mishima-gun; Toshiharu Matsumiya, Shinnanyo, both of Japan

[73] Assignees: Sekisui Kagaku Kogyo Kabushiki Kaisha, Osaka; Japan Immuno Research Laboratories Co., Ltd., Takasaki, both of Japan

[21] Appl. No.: 610,067

[22] Filed: Feb. 29, 1996

[51] Int. Cl.⁶ .............................. B05D 3/10; B05D 3/02; B05D 1/38
[52] U.S. Cl. .......................... 427/2.12; 427/2.1; 427/2.3; 427/307; 427/243; 427/222
[58] Field of Search .................................. 427/307, 308, 427/2.12, 2.3, 2.25, 2.1, 372.2, 235, 243, 244, 222; 210/500.23; 604/408; 264/209.1, 177.18

[56] References Cited

U.S. PATENT DOCUMENTS

| | | | |
|---|---|---|---|
| 3,423,491 | 1/1969 | McLain et al. | 264/209.1 |
| 4,020,230 | 4/1977 | Mahoney et al. | 264/289.6 |
| 4,169,051 | 9/1979 | Satoh et al. | 210/679 |
| 4,560,720 | 12/1985 | Aoyagi et al. | 604/408 |
| 4,612,340 | 9/1986 | Ohachi | 604/408 |
| 4,613,441 | 9/1986 | Kohno et al. | 210/500.36 |
| 4,670,013 | 6/1987 | Barnes et al. | 604/403 |
| 4,744,899 | 5/1988 | Tani et al. | 210/263 |
| 4,994,273 | 2/1991 | Zentner et al. | 424/422 |
| 5,063,009 | 11/1991 | Mizutani et al. | 264/49 |
| 5,077,222 | 12/1991 | Lau | 436/88 |
| 5,336,329 | 8/1994 | Langenmayr | 134/7 |

*Primary Examiner*—Diana Dudash
*Attorney, Agent, or Firm*—Armstrong, Westerman, Hattori, McLeland & Naughton

[57] ABSTRACT

A method of preparing a carrier for a blood treatment apparatus includes the steps of dipping a carrier containing about 10 to about 100 parts by weight of a plasticizer with respect to 100 parts by weight of thermoplastic resin in a solvent dissolving only the plasticizer without dissolving the thermoplastic resin thereby extracting the plasticizer, thereafter dipping the carrier in an aqueous solution of about pH 5 to about pH 9, and then drying the same to retain the solute of the aqueous solution in the pores of the resin.

6 Claims, No Drawings

METHOD OF PREPARING CARRIER FOR BLOOD TREATMENT APPARATUS

BACKGROUND OF THE INVENTION

1. Field of the Invention

The present invention relates to a method of preparing a carrier for a blood treatment apparatus which can be preferably employed as a carrier for an extracorporeal circulation system for extracorporeally circulating human blood and treating the same, and more particularly, it relates to a method of preparing a carrier for a blood treatment apparatus which can effectively suppress hemolysis in employment.

2. Description of the Related Art

Extracorporeal circulation is generally employed for removing an undesirable component such as waste from blood or extracting a component contained in the blood. In such extracorporeal circulation, a column for treating the blood is inserted in an intermediate portion of a blood circuit which is connected to the organism. This column is charged with a carrier for adsorbing or sticking a target component which is contained in the blood.

For the aforementioned purpose, various types of carriers such as fibrous and granular carriers are employed in general. The fibrous carriers are made of nylon fiber, polyester fiber and the like, for example, while the granular carriers are made of polystyrene, cellulose acetate or polyethylene terephthalate, polypropylene terephthalate and the like, for example. These carriers are disclosed in Japanese Patent Laying-Open No. 2-193069 (1990), for example.

In order to apply such a carrier to medical care in practice, it is necessary to sterilize the carrier after charging the same in the column. While the carrier is sterilized by hyperbaric steam sterilization, hot-air sterilization, sterilization with ethylene oxide gas, gamma-ray sterilization or electron beam sterilization, every such method is adapted to apply energy to or cause chemical change of the carrier. Consequently, there are some possibilities that liberation of end groups of the carrier or denaturation of the carrier are caused.

SUMMARY OF THE INVENTION

An object of the present invention is to provide a method of preparing a carrier for a blood treatment apparatus which hardly causes liberation or denaturation of end groups upon any sterilization, to attain excellent safety.

According to a wide aspect of the present invention, provided is a method of preparing a carrier for a blood treatment apparatus comprising the steps of dipping a carrier containing 100 parts by weight of thermoplastic resin and about 10 to about 100 parts by weight of a plasticizer in a solvent dissolving the plasticizer without dissolving the thermoplastic resin thereby extracting the plasticizer, dipping the carrier in an aqueous solution of about pH 5 to about pH 9 after extracting the plasticizer, and drying the carrier after dipping the same in the aqueous solution.

According to the present invention, a carrier consisting of the thermoplastic resin and having pores or clearances is formed by the step of dipping the carrier in the solvent dissolving the plasticizer without dissolving the thermoplastic resin for extracting the plasticizer, while solute or gel of the aqueous solution for pH adjustment homogeneously adheres into the pores or clearances by the step of dipping the carrier in the aqueous solution of about pH 5 to about pH 9. Therefore, denatured end groups or free radicals of the thermoplastic resin caused by later sterilization or preservation of the carrier are neutralized by the solute or the gel, whereby hemolysis can be effectively suppressed.

The thermoplastic resin employed in the present invention is not particularly restricted but can be prepared from cellulose, cellulose acetate, polymethyl methacrylate, ethylene-vinyl alcohol copolymer, polyacrylonitrile, polysulfone, polycarbonate or polystyrene, for example.

On the other hand, the plasticizer employed in the present invention can be prepared from acetyl triethyl citrate (ATEC), dioctyl phthalate (DOP), diethyl phthalate (DEP) or epoxidized soybean oil, for example.

According to the present invention, the carrier containing the thermoplastic resin and the plasticizer is first prepared. This carrier is obtained by adding about 10 to about 100 parts by weight of the plasticizer to 100 parts by weight of the thermoplastic resin and molding the mixture into a desired shape. The carrier is not restricted in shape but may be provided in a proper shape, such as a beady shape, a plate shape or a fibrous shape, for example, which is generally employed for a carrier for a blood treatment apparatus. Further, the carrier can be molded into the desired shape by a proper molding method such as injection molding or extrusion molding.

The plasticizer is added at the ratio of about 10 to about 100 parts by weight with respect to 100 parts by weight of the thermoplastic resin, since an excessive amount of pores or clearances are defined by extraction of the plasticizer to reduce the strength of the obtained carrier if the amount of the plasticizer exceeds about 100 parts by weight. If the amount of the plasticizer is less than about 10 parts by weight, on the other hand, the amount of the defined pores or clearances is so small that the solute of the aqueous solution of about pH 5 to about pH 9 too insufficiently adheres into the pores or clearances to attain the object of the present invention. Thus, the plasticizer is employed in the range of about 10 to about 100 parts by weight with respect to the thermoplastic resin, as described above.

According to the present invention, the aforementioned carrier is dipped in the solvent which dissolves the plasticizer without dissolving the thermoplastic resin. This solvent can be prepared from a proper solvent which is selected in response to the type of the carrier so that the same can dissolve only the employed plasticizer without dissolving the thermoplastic resin forming the carrier, such as acetone, methyl ethyl ketone, octyl alcohol, tetrahydrofuran, methanol or ethanol, for example.

While the step of dipping the carrier in the solvent is not particularly restricted, the solvent is preferably prepared in a sufficient amount with respect to that of the carrier, in order to reliably extract the plasticizer from the carrier. The time for dipping the carrier in the solvent is about 1 hour to 1 week, while the same is not particularly restricted so far as the plasticizer can be sufficiently extracted.

Due to the aforementioned dipping, the plasticizer is eluted from the carrier, thereby defining a constant amount of pores or clearances in the carrier. In this case, the pores or clearances are preferably homogeneously distributed in the overall carrier so that the carrier is not collapsed by the bloodstream in extracorporeal circulation. The amount of the plasticizer is set in the aforementioned range for this purpose.

Then, the carrier provided with the pores or clearances is dipped in the aqueous solution of about pH 5 to about pH 9, so that the aqueous solution is incorporated into the pores or clearances. Thereafter the carrier is dried so that only the solute or the gel homogeneously adheres into the pores or clearances.

The carrier can be dried under heating, or being left at the ordinary temperature. When heating is employed, the carrier is preferably heated at a temperature which is lower than the softening point of the thermoplastic resin forming the carrier, and more preferably dried under reduced pressure, so that the carrier can be more quickly dried.

The solute of the aqueous solution can be prepared from proper solute, such as sodium hydrogencarbonate, sodium carbonate, magnesium oxide, sodium hydroxide, boric acid or sodium phosphate, for example, so far as the same can attain a pH value of about 5 to about 9. The pH of the blood is acidified if the pH value of the aqueous solution dissolving the solute is too low, while the former is alkalinized if the latter is too high. Thus, the pH value of the aqueous solution is set in the range of about 5 to about 9.

The carrier for a blood treatment apparatus obtained according to the present invention can be generally employed for application which must adsorb or stick blood components in a blood treatment apparatus other than that for an extracorporeal circulation system with no hemolysis, in addition to the application to be charged in the aforementioned column for extracorporeal circulation.

The foregoing and other objects, features, aspects and advantages of the present invention will become more apparent from the following detailed description of the present invention.

DESCRIPTION OF THE PREFERRED EMBODIMENTS

Nonrestrictive Example of the present invention is now described, to clarify the present invention.

EXAMPLE 1

A cellulose acetate pellet ("ASETIPERETTO" (trade name) by DAISEL CRAFT Cop.) containing 30 percent by weight (43 parts by weight of ATEC to 100 parts by weight of cellulose acetate is used) was polished to prepare beads of 2 mm in particle size. The plasticizer was extracted from 25 kg of the obtained beads with 80 liters of methanol, and this operation was repeated 5 times. The extraction temperature was 60° C., which is slightly lower than the boiling point of methanol, and single extraction was performed for 2 hours. Thus, clearances or pores of 30% in weight ratio were defined in the cellulose acetate beads.

The beads were vacuum dried until the methanol content in these beads was not more than 0.5 percent by weight. Thereafter, a step of dipping the beads in 80 liters of pure water containing 0.025 percent by weight of sodium hydrogencarbonate at 50° C. (pH value of this solution is 6.4) was repeated 6 times. The single dipping time was 1.5 hours. As the result, the beads were impregnated with the sodium hydrogencarbonate of about 0.0038% with respect to the dry weight of the beads. Then, the beads were dried at 85° C. to evaporate the pure water, thereby obtaining a beady carrier.

220 g of this carrier was charged in a column with addition of 150 ml of a physiological salt solution, and subjected to hyperbaric steam sterilization at 121° C. for 20 minutes. The pH value of the column content was 4.3 to 4.4 after the sterilization. After a pretreatment for applying the carrier to extracorporeal circulation in practice, the pH value of the column content was 5.0 to 5.3, in a state causing no hemolysis upon application to extracorporeal circulation.

COMPARATIVE EXAMPLE 1

A beady carrier was prepared similarly to Example 1 except that pure water was employed in place of that containing 0.025 percent by weight of sodium hydrogencarbonate, charged in a column, and subjected to hyperbaric steam sterilization. The pH value of the column content was 3.9 after the sterilization. After a pretreatment for applying the carrier to extracorporeal circulation in practice, the pH value of the column content was 4.4 to 4.7, in a state causing hemolysis upon application to extracorporeal circulation.

Although the present invention has been described in detail, it is clearly understood that the same is by way of illustration and example only and is not to be taken by way of limitation, the spirit and scope of the present invention being limited only by the terms of the appended claims.

What is claimed is:

1. A method of preparing a carrier for a blood treatment apparatus, which consists essentially of:

forming pores in a thermoplastic resin by dipping the thermoplastic resin, containing about 10 to about 100 parts by weight of a plasticizer per 100 parts of the thermoplastic resin, in a solvent to dissolve the plasticizer without dissolving the thermoplastic resin;

dipping the thermoplastic resin from which the plasticizer has been removed in an aqueous solution containing a solute at a pH of about 5 to about 9; and drying the thermoplastic resin, which has been dipped in the aqueous solution, leaving solute from the aqueous solution in the pores of the thermoplastic resin.

2. The method according to claim 1, wherein the thermoplastic resin is cellulose, cellulose acetate, polymethyl methacrylate, poly(ethylene-vinyl alcohol), polyacrylonitrile, polysulfone, polycarbonate or polystyrene.

3. The method according to claim 1 or 2, wherein the plasticizer is acetyl triethyl citrate, dioctyl phthalate, diethyl phthalate or epoxidized soybean oil.

4. The method according to claims 1 or 2, wherein the solvent is acetone, methyl ethyl ketone, octyl alcohol, tetrahydrofuran, methanol or ethanol.

5. The method according to claim 1, wherein the carrier is in the form of beads.

6. The method according to claim 1, wherein the carrier is in the form of beads, and which further comprises placing the carrier in a column and adjusting the pH of the carrier in the column to a pH of 5.0 –5.3.

* * * * *